United States Patent [19]

Girling

[11] Patent Number: 5,877,409
[45] Date of Patent: Mar. 2, 1999

[54] METHOD AND SYSTEM FOR DETERMINING VISCOSITY INDEX

[75] Inventor: Peter Michael Girling, Coplay, Pa.

[73] Assignee: Mobil Oil Corporation, Fairfax, Va.

[21] Appl. No.: 870,641

[22] Filed: Jun. 6, 1997

[51] Int. Cl.$^6$ .................................................. G01N 11/08
[52] U.S. Cl. ........................................ 73/54.06; 73/54.42
[58] Field of Search ............................... 73/54.05, 54.06, 73/54.09, 54.42

[56] References Cited

U.S. PATENT DOCUMENTS 4,627,271 12/1986 Abbott et al. ............................ 73/54.06
4,790,668 12/1988 Seyed-Yagoobi ....................... 73/54.06

*Primary Examiner*—Michael Brock
*Attorney, Agent, or Firm*—Malcolm D. Keen

[57] ABSTRACT

A method and system for determining the viscosity index of a petroleum liquid. The determination may be made on a single, discrete sample or on a continuous sample stream. A sample is fed into a first pressure drop device where a first pressure drop is measured. A first sample temperature and mass flow are measured at that point. A first density of the sample is determined from a sample mass flow meter so that a first kinematic viscosity can then be determined using the first sample pressure drop, temperature, and density. Then the sample temperature is changed to a second sample temperature and the sample is passed through a second pressure drop device. The second sample temperature, sample density and pressure drop are used to determine a second kinematic viscosity at the second sample temperature. The viscosity index of the sample is determined using the first kinematic viscosity and the second kinematic viscosity. The viscosity index of the sample is presented in digital form to system operators.

6 Claims, 1 Drawing Sheet

METHOD AND SYSTEM FOR DETERMINING VISCOSITY INDEX

BACKGROUND OF THE INVENTION

The present invention relates to a method and system for determining the viscosity and the viscosity index of a product. More particularly, the present invention relates to a method and system for sampling a stream, e.g., petroleum product stream, and for automatically determining the viscosity at any temperature and the viscosity index (VI) of the petroleum product.

Dynamic viscosity can be determined by measuring the force required to overcome fluid friction in a film of known dimensions. Dynamic viscosity is usually reported in centipoise or Pascal seconds (Pas) (1 cP=$10^{-3}$ Pas) and is determined using well known equations such as Poiseuille equation:

$$\mu = \frac{1.472 * 10^5 d^4 \Delta p}{QL}$$

wherein $\mu$=absolute (dynamic) cP d=inner dia of conduits, mm,

L=length of segments, mm,

Q=flow rate in conduits, ml/min, and $\Delta$p=press drop across segments, bars.

L and d are fixed, Q may be fixed or measured, and dp is measured. For a given L, d and Q, Viscosity is a constant times the $\Delta$p.

Kinematic viscosity is a measure or timing of the flow driven by gravity, and is the viscosity most often use in a laboratory. Dynamic viscosities, in centipoise, can be converted to kinematic viscosities, in centistokes (cSt), by dividing by the density in grams per cubic centimeter (g/cm$^3$) at the same temperature. The kinematic viscosity unit is mm$^2$/sec or centistokes.

The viscosity of a fluid usually increases as temperature is decreased, and decreases as the temperature is increased. Viscosities of oils at temperatures other than the temperature at which they are measured can be determined by measuring the viscosities at two temperatures, then plotting these points on viscosity-temperature charts developed by ASTM and issued as standard ASTM D341 which is incorporated herein by reference. A straight line is drawn through these two points, and viscosities at other temperatures are read along this line.

Different oils have different rates of change of viscosity with temperature. Viscosity Index (VI) is a method of representing this rate of change, based on a comparison with the relative rates of change of two arbitrarily selected types of oils that differ widely in this characteristic. A high VI indicates a relatively low rate of change of viscosity with temperature. Conversely, a low VI indicates a relatively high rate of change of viscosity with temperature.

VI is commonly associated with petroleum products such as crude oils, lubricating oils and their constituent base stocks. It is one of the most important specifications that must be met when determining the suitability of a particular oil for a given use. This characteristic is important because many oils are expected to operate not at some fixed temperature but over a range of temperatures. For example in the case of an automobile engine, a lubricating oil is expected to perform properly over a potentially very wide range of ambient and operating temperatures. These temperatures can vary from below freezing to the very high temperatures observed in tropical zones.

An ASTM standard provides a widely used scale for reporting VI. The scale is an empirical one based on the arbitrary assignment of VI values to two different kinds of crude oils. The viscosity-temperature relationship of a Pennsylvania crude was arbitrarily assigned a VI of 100. That same relationship for a Gulf Coast crude was assigned a value of 0. Some lubricating oils particularly synthetic oils may have a VI below 0 or above 100. The use of additives can increase observed VI to well over 100.

This method for measuring the VI of an oil is the standard described in ASTM D 2270-91 which is incorporated herein by reference. This standard describes a method for determining the VI of petroleum products using their kinematic viscosities at 40° C. and 100° C. For oils of Viscosity Index up to and including 100, VI may be calculated using the equation:

$$VI=[(L-U)/(L-H)]\times 100$$

where

L is the kinematic viscosity at in cS (mm$^2$ sec$^{-1}$) at 40° C. of an oil of 0 viscosity index having the same kinematic viscosity at 100° C. as the oil whose viscosity index is to be calculated, H is the kinematic viscosity at in cS (mm$^2$ sec$^{-1}$) at 40° C. of an oil of 100 viscosity index having the same kinematic viscosity at 100° C. as the oil whose viscosity index is to be calculated, U is the kinematic viscosity at 40° C. of the sample oil.

For oils having a VI over 100, equation I does not give reliable results and an alternate procedure detailed in ASTM D 2270 must be followed. The use of the ASTM method requires maintaining constant sample temperatures at the 40° C. and 100° C. points while viscosity measurements are made. Thus, the ASTM procedure can require expensive constant temperature bath equipment and a great deal of time to produce results. Much of that time required is devoted to taking a sample from constant initial temperature of 40° C. to a constant 100° C. For the process operator desiring rapid VI information that could be of use to monitor product quality during manufacture, this delay is unacceptable.

Devices are known for measuring viscosity. However, none provide direct information concerning the VI of the liquid or other substance being tested. In view of the importance of VI to users of petroleum products, particularly lubricating oils, there is a need for a device that provides direct, continuous information concerning VI.

SUMMARY OF THE INVENTION

Therefore it is an object of this invention to provide a method and an system for the continuous measurement of viscosity index of a homogenous hydrocarbon liquid.

It is another object of this invention to provide a method of determining viscosity index without the need for or use of sample baths at a constant fixed temperature.

Still another object of this invention is to provide a method for measuring Viscosity Index using viscosity measurements made at or near the temperature of a process stream.

In accordance with a broad aspect of the present invention there is provided a method for continuously measuring the viscosity index (VI) of a liquid hydrocarbon stream. The method comprises feeding the hydrocarbon stream through a first length of a conduit, and generating a first signal representative of the temperature of the streams in the first length. A second signal is generated that is representative of the pressure drop ($\Delta p1$) across at least a segment of the first length of the conduit. Then the temperature of the stream is changed, e.g., by a heat exchanger, and the stream is fed through a second length of the conduit. A third signal is generated that is representative of the temperature of the stream in the second length, and a fourth signal is generated that is representative of the pressure drop ($\Delta p2$) across at least a segment of the second length of the conduit. The first, second, third and fourth signals are directed to computing means for executing a program for generating a slope of a line defined by logarithm of dynamic viscosity ($v_1, v_2$) versus the inverse of temperature of the hydrocarbon stream in the first and second conduits. The slope is an indication of VI. Also, this slope provides the viscosity of the sampled stream at any temperature within the limits of the ASTM standards. Further, this slope permits the determination of the temperature at which the stream would be at a desired viscosity.

If the density of the stream is measured at both temperatures, or the density is measured at one temperature and extrapolated to the second temperature by known means, it is possible to convert the dynamic viscosity to kinematic viscosity at both temperatures. In this way, it is possible to predict the dynamic viscosity or the kinematic viscosity at any other temperature.

Using the predicted kinematic viscosities at 40° C. and 100° C., the method of ASTM D 2270 can be used to calculate the viscosity index.

In accordance with another broad aspect of the present invention there is provided a system for continuously measuring the viscosity index (VI) of liquid hydrocarbon stream comprising means for feeding a hydrocarbon stream through a conduit, means for generating a first signal representative of the temperature of the stream in a first length of the conduit, and means for generating a second signal representative of the pressure drop ($\Delta p1$) across at least a segment of the first length of the conduit. Means, downstream of the first length, are provided for changing the temperature of the stream. The system also comprises means for generating a third signal representative of the temperature of the stream in a second length of the conduit, and means for generating a fourth signal representative of the pressure drop ($\Delta p2$) across at least a segment of the second length of the conduit. Means are provided for directing the first, second, third and fourth signals to computing means for executing a program for determining a slope in response to the first, second, third and fourth signals.

The computing means, using the slope, generates a signal representative of the VI of the liquid hydrocarbon stream by calculating values of kinematic viscosity at 40° C. and at 100° C. or at any other desired temperature. From these calculated values of viscosity a signal representative of the VI is generated using the ASTM standard procedure.

In accordance with an other aspect of the present invention the slope is defined by known functions such as:

$$\text{slope} = \frac{\log \Delta p_1 - \log \Delta p_2}{1/T_1 - 1/T_2}$$

wherein
$\Delta p_1$=pressure drop-first conduit (bars),
$\Delta p_2$=pressure drop-second conduit (bars),
$T_1$=absolute temperature-first slip-stream portion,
$T_2$=absolute temperature-second slip-stream portion.

The slope may also be derived from the mathematical relationships in the appendixes of ASTM D 341-89 which is incorporated herein by reference. The general relationship from the appendixes is:

$$\log\log Z = A - B \log T$$

wherein
$z = (V + 0.7 + C - D + E - F + G - H)$;
log=logarithm to base 10;
v=kinematic viscosity,cSt (or mm$^2$/s);
T=temperature, K or °R;
A&B=constants; and
terms C through H are exponentials on the natural base e and are listed in the appendixes of ASTM D 341-89.

The liquid hydrocarbon stream may be a slurry. However, it is preferred that the hydrocarbon stream be homogeneous. Also the hydrocarbon stream may be sampled or a slip-stream may be provided to feed a sample stream through first and second conduit portions having means for changing the stream temperature therebetween.

The signal strength of the $\Delta p$ signals will be increased or enhanced by reducing the diameter of the portions. Therefore, a small diameter conduit such as a capillary is preferred to the conduit portions. Although not necessary, the segment of the second conduit is preferably similar in relative location, construction and size as the segment of the first conduit to simplify the method for determining the desired measurements.

An aspect of the present invention is that the flow and temperature are measured accurately. However, the flow and temperature do not need to be precisely controlled as required by prior art viscometers.

Thus, the present invention overcomes the disadvantages of the prior art and attains the objects of the invention by providing a rapid, continuous, and accurate means for determining the viscosity or the Viscosity Index of a petroleum product. The present invention also avoids the need for expensive, bulky constant temperature bath equipment by directly measuring the stream or by using a relatively small, continuous sample drawn directly from a process stream. The temperature of such a sample is easy to maintain and can be raised or lowered with a minimum of effort and time. This aspect of the invention permits the necessary viscosity determinations to be made at or near process temperatures or at any convenient temperature. The invention offers the further advantage of providing process system operators timely information concerning the Viscosity Index of the process medium.

DESCRIPTION OF SPECIFIC EMBODIMENTS

The VI of an oil is calculated from viscosities determined at two temperatures by means of tables published by ASTM in standard D 2770-91. ASTM D 2770-91 is incorporated herein by reference. Tables based on viscosities determined at both 100° F. and 212° F., and 40° C. and 100° C. are available in this standard.

The present invention provides a process analyzer to measure viscosity at two temperatures, to calculate the viscosity values at 40° C. and 100° C., and to calculate the Viscosity Index using data from published tables that are stored in a computer.

Figure 1:
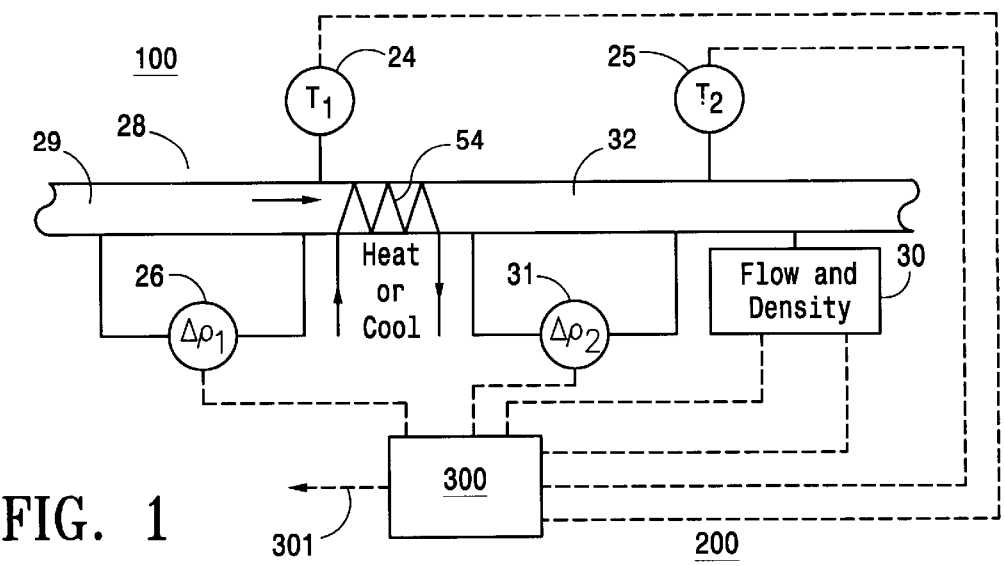
FIG. 1 is a schematic view of a first embodiment of the invention wherein a conduit is directly sampled.

With reference to FIG. 1, an input end 100 of the system is designed to work at one of a high or a low temperature such as near 100° C. or near 40° C., and includes a conduit 28, means 24 for measuring the temperature of the fluid in the conduit 28, means 26 for measuring the pressure loss across a segment 29 of the conduit, and means 54 for heating or cooling the sample fluid to the other of the high and the low temperatures such as near 100° C. or near 40° C.

An output end 200 of the system is connected in series with the input end 100. The output end 200 includes means 31 for measuring the pressure differential across a second 32 segment of the conduit 28. Also provided is means 30 for measuring the flow of the fluid in the conduit, such as mass or volume flow of the sample, and also the density of the stream in the conduit 28. Computing means 300 are provided for calculating the Viscosity Index from the data obtained and presenting it as an electrical output signal 301. The output signal 301 can be used as a feed-back or feed-forward control signal such as in the blending of lubricating oils.

Figure 2:
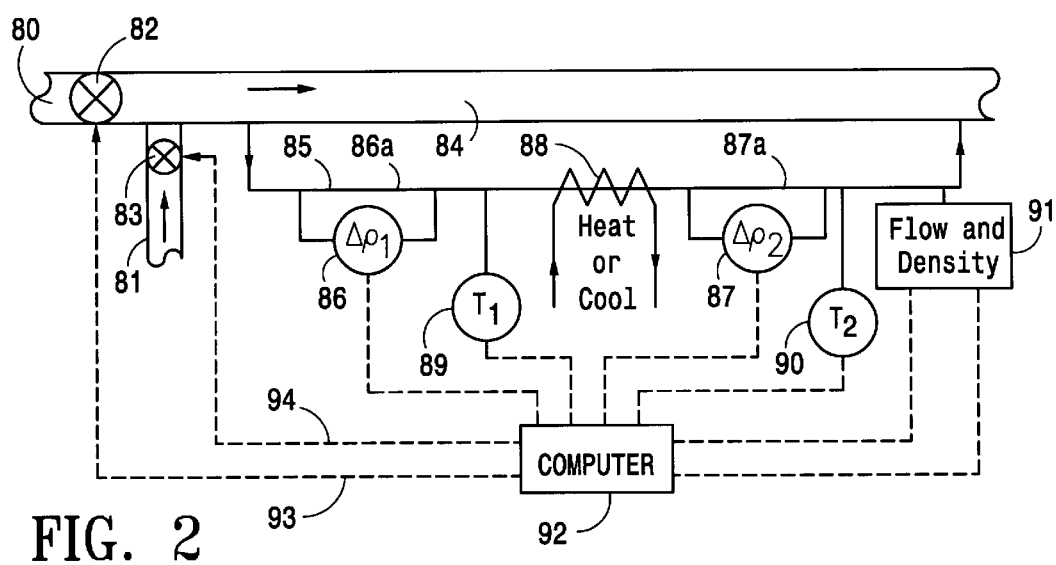
FIG. 2 is a schematic representation of a second embodiment of the invention wherein a slip-stream of a main stream is monitored.

FIG. 2 is a schematic of a lubricating blending system comprising feed conduits 80, 81 with lubricating oils of different VI's and having valves 82, 83 therein for controlling the relative amounts of the lubricating oils blended in a main conduit 84. The blend of lubricating oils in the main conduit 84 is continuously sampled through a slip-stream 85. A first pressure differential device 86 measures the pressure drop across a first segment 86a of the slip-stream, and a second pressure differential device 87 measures the pressure drop across a second segment 87a of the slip-stream. A heat exchanger 88 is provided between the first and second segments of the slip-stream 85 for heating or cooling the stream of blended lubricating oil therein.

As in FIG. 1, the embodiment of FIG. 2, also includes temperature sensors 89, 90, and a flow and density meter 91. Components 30 and 91 are suitably coriolis effect or mass flow meters which provide flow and density output signals. The signal outputs of the first and second pressure differential devices 86, 87, the temperature sensors 89, 90, and the flow and density meter 91 are fed to a computer 92 wherein output control signals 93, 94, are generated for adjusting the valves 83, 83 to provide a blended stream in the main conduit 84 having a predetermined VI.

As discussed above, the Viscosity Index is used to measure the variation in kinematic viscosity due to changes in the temperature of a petroleum product between 40° C. and 100° C.

If the kinematic viscosity of the oils at 100° C. is less than or equal to 70 mm$^2$/s (cSt), extract from a Table of data in ASTM standard D220-91 the corresponding values for L and H. Measured values that are not listed, but are within the range of the Table, may be obtained by linear interpolation. The viscosity index is not defined and may not be reported for oils of kinematic viscosity of less than 2.0 mm$^2$/s (cSt) at 100° C.

If the kinematic viscosity is above 70 mm$^2$/s (cSt) at 100° C., calculate the values of L and H as follows:

$$L = 0.8353\ Y^2 + 14.67\ Y - 216$$

$$H = 0.1684\ Y^2 + 11.85\ Y - 97$$

where:

L is the kinematic viscosity in cS (mm$^2$ sec$^{-1}$) at 40° C. of an oil of 0 viscosity index having the same kinematic viscosity at 100° C. as the oil whose viscosity index is to be calculated, H is the kinematic viscosity in cS (mm$^2$ sec$^{-1}$) at 40° C. of an oil of 100 viscosity index having the same kinematic viscosity at 100° C. as the oil whose viscosity index is to be calculated, Y is the kinematic viscosity, in cS (mm$^2$ sec$^{-1}$), at 100° C. of the oil whose viscosity index is to be calculated.

Calculate the viscosity index, VI, of the oil as follows:

$$VI = [(L-U)/(L-H)]100$$

where:

U = kinematic viscosity, in mm$^2$/s (cSt), at 40° C. of the oil whose viscosity index is to be calculated.

Figure 3:
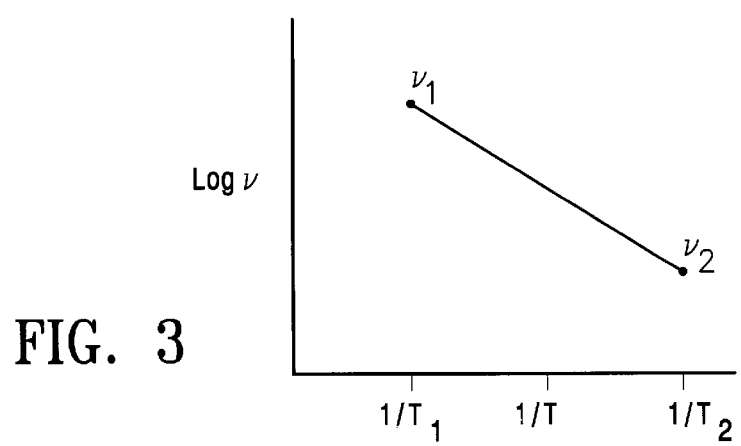
FIG. 3 is a plot of viscosity v. temperature at 40° C. and 100° C.

FIG. 3 is a graph which illustrates the principles involved calculating viscosity in accordance with the present invention. The computer 92 generates a slope of a line defined by logarithm of dynamic or kinematic viscosity ($v_1, v_2$) versus the inverse of temperature of the hydrocarbon stream in the first and second segments. The point $v_2$ represents the kinematic viscosity of the actual sample at 100° C., and, by definition, hypothetical samples of viscosity index 0 and 100 respectively which have the same viscosity as the real sample at 100° C. The point $v_1$ is the kinematic viscosity of the actual at 40° C. Thus, the FIG. 3 graph shows the relationship between the log to base 10 of viscosity and the inverse of temperature as being nearly linear.

With accurate temperature measurements, ASTM standard provides a method for providing required viscosities from values obtained at different temperatures. Equations are also provided in this ASTM standard for determining values by interpolation or extrapolation. This determination method is limited to homogeneous hydrocarbon liquids. Asphalt or bitumen can be determined by ASTM standard for asphalts and bitumens i.e. ASTM-D 2493.

In an embodiment of the invention, there is provided a method and an analyzer for determining VI by measuring the pressure drop across a first segment of a conduit, changing the sample temperature downstream of the first segment, and measuring the pressure drop across a second segment of the conduit downstream of the temperature change.

The computer is programmed with the relationship between viscosity and temperature which approximates to:

$$\log v = A + B/T$$

where:

T = Absolute Temperature,

A & B = empirical contents which drop out when resolving the equation.

For two viscosities at two temperatures:

$$\text{slope} = \frac{\log v_1 - \log v_2}{1/T_1 - 1/T_2} = \frac{\log v_1/v_2}{1/T_1 - 1/T_2}$$

For oils at 40° C. and at 100° C., $3 < V_1/V_2 < 20$.

If $d_1 = d_2$, and $L_1 = L_2$ by using two identical conduits, and Q cancels out, then $v_1/v_2 = \Delta p_1/\Delta p_2$, and $$\text{slope} = \frac{\log \Delta p_1 - \log \Delta p_2}{1/T_1 - 1/T_2}$$

wherein $\Delta p_1$=pressure drop-first conduit (bars), $\Delta p_2$=pressure drop-second conduit (bars), $T_1$=absolute temperature-first slip-stream portion, $T_2$=absolute temperature-second slip-stream portion.

The outputs of the four measuring devices 86, 87, 89, 90 (FIG. 1) are inputed to a computer, and the slope is determined therein. This slope gives an indication of the VI which can be used for process control without further calculation or processing.

Thus, in this embodiment flow rate is not used because when two conduits with the same diameter and length, the flow rate drops out of the equation. Therefore, only two differential pressures and the two temperatures need to be measured to give the slope in accordance with equation I.

As noted above, viscosity index (VI) is a widely used and accepted measure of the effect of temperature on viscosity, and is used in blending of hydrocarbon streams. VI is used for characterizing homogeneous hydrocarbon oils, and can also be used to specify asphalts and bitumens.

A second embodiment of the invention relies on a knowledge of mass flow and conduit characteristics to determine kinematic viscosity before calculating the Viscosity Index. Sample flow rate and temperature are measured accurately and are controlled approximately. This method is based on recognition of an approximate relationship between viscosity and temperature of ASTM/API standard: Log v=A+B/T Again with reference to FIG. 2, the is shown a method and system for continuously measuring the viscosity index (VI) of a liquid hydrocarbon stream comprising feeding the hydrocarbon stream through a first segment 86a of a slip-stream conduit 85. Temperature sensing means 89 generates a first signal representative of a temperature ($T_1$) of the stream in the first segment, and pressure sensing means 86 generates a second signal representative of the pressure drop ($\Delta p1$) across at least a portion of the first segment of the conduit. Means 88 are provided for changing the temperature of the hydrocarbon stream, and for feeding the hydrocarbon stream through a second segment of the conduit. Second temperature sensing means 90 generates a third signal representative of the temperature ($T_2$) of the hydrocarbon stream in the second segment 87a, and second pressure sensing means 87 generates a fourth signal representative of the pressure drop ($\Delta p2$) across at least a portion of the second segment 87a of the conduit. A single sensor 91 or separate sensors (not shown) generates a fifth signal representative of the flow rate of the hydrocarbon stream in the conduit 85, and a sixth signal representative of the density of the hydrocarbon stream. The first, second, third, fourth, fifth and sixth signals are directed to computing means 92 for executing a program for calculating a first dynamic viscosity ($v_1$) of the hydrocarbon stream and a second dynamic viscosity ($v_2$) of the hydrocarbon stream, each one of the dynamic viscosities being defined by:

$$\mu = \frac{1.472 * 10^5 d^4 \Delta p}{QL}$$

where $\mu$=dynamic viscosity, cP d=inner dia of conduits, mm,

L=length of segments, mm,

Q=flow rate in conduits, ml/min, and $\Delta p$=press drop across segments, bars.

The dynamic viscosities are converted to kinematic viscosities. ASTM D341 equations stored in a memory of the computing means 92 are used to extrapolating the first kinematic viscosity to one of 40° C. and 100° C. and extrapolating the second kinematic viscosity to the other of 40° C. and 100° C. ASTM D2270 basic values for L and H for kinematic viscosity in 40°–100° C. system stored in the memory of the computing means are used to determine the VI of said hydrocarbon stream in accordance with:

$$VI = \frac{L - U}{L - H} * 100$$

wherein

L=v at 40° C. of the VI 0 oil, cSt or $mm^2/s$,

H=v at 40° C. of the VI 100 oil, cSt or $mm^2/s$, and

U=v at 40° C. of said liquid hydrocarbon stream, cSt or $mm^2/s$.

The computing means 92 generates a signal representative of the VI of the liquid hydrocarbon stream, and an output signal 93 to control blending of two streams by selective operation of one or both of valves 82,83.

The sample should remain at a constant temperature through each of the two segments 86a,87a of the conduit. The measurements of mass flow of the sample should be as accurate as possible. One of the conduits may be maintained at a temperature near 100° C. and the other may be near 40° C. However, these conduit temperatures may be at any two different temperatures. The pressures across the two conduits are accurately measured using differential pressure transmitters.

Typically, the analyzer system of the present invention will monitor a slip stream having viscosities between about ≦2000 cP at 40° C. and about ≧2 cP at 100° C.

The sample liquid is moved through the conduits by the pressure drop between the sample inlet and outlet. The differential pressure $\Delta p$ across each length or segment of the conduit is suitably between about 80 inches W.C. to about 1000 inches W.C. The pressure drop may be supplied by mechanical means such as a pump. The sample flow rate to generate this differential depends upon the diameter of the conduit.

The temperature of the sample may be changed by applying heat in the form of steam or other hot fluids or electricity, and may be cooled by cooling water or other cooling apparatus. The temperature is changed at a location 54,88 between the two conduits.

The temperature is measured using an accurate temperature device 24,25;86,87 such as a Resistance Temperature Detector (RTD) probe inserted in the conduit.

The mass flow of the sample and its density are measured by a mass flow meter 30,91 located anywhere in the stream, for example, before the sample stream enters the heat exchanger 88 which is typically heated by steam. The sample then flows through the second segment of the conduit 85.

If the sample is supplied at the higher temperature, e.g. around 100° C., the flow schematic is similar to that described above but re-arranged slightly so that the mass flowmeter 30,91 still operates at any suitable temperature and steam heating is replaced by water cooling.

Although the present invention has been described with preferred embodiments, it is to be understood that modifications and variations may be utilized without departing from the spirit and scope of this invention, as those skilled in the art will readily understand. Such modifications and variations are considered to be part of the invention, provided they come within the scope of the appended claims and their equivalents.

What is claimed is:

1. A method for continuously measuring the viscosity index (VI) of liquid hydrocarbon stream comprising:

feeding a said hydrocarbon stream through a first segment of a conduit;

generating a first signal representative of the temperature of the stream in the first segment;

generating a second signal representative of the pressure drop ($\Delta p1$) across at least a portion of the first segment;

changing the temperature of the stream;

feeding said hydrocarbon stream through a second segment of the conduit;

generating a third signal representative of the temperature of the stream in said second segment;

generating a fourth signal representative of the pressure drop ($\Delta p2$) across at least a portion of the second segment of the conduit;

directing the first, second, third and fourth signals to computing means and executing a program for determining a slope in response to the first, second, third and fourth signals;

with said computing means and program, generating a signal representative of the VI of said liquid hydrocarbon stream from said slope.

2. The method of claim 1 wherein said slope is defined by:

$$\text{slope} = \frac{\log \Delta p_1 - \log \Delta p_2}{1/T_1 - 1/T_2}$$

wherein $\Delta p_1$=pressure drop-first conduit (bars), $\Delta p_2$=pressure drop-second conduit (bars), $T_1$=absolute temperature-first slip-stream portion, $T_2$=absolute temperature-second slip-stream portion.

3. A method for continuously measuring the viscosity index (VI) of a liquid hydrocarbon stream comprising:

feeding said hydrocarbon stream through a first segment of a conduit;

generating a first signal representative of a temperature ($T_1$) of the stream in the first segment;

generating a second signal representative of the pressure drop ($\Delta p1$) across at least a portion of the first segment of the conduit;

changing the temperature of the hydrocarbon stream;

feeding the hydrocarbon stream through a second segment of the conduit;

generating a third signal representative of the temperature ($T_2$) of the hydrocarbon stream in the second segment;

generating a fourth signal representative of the pressure drop ($\Delta p2$) across at least a portion of the second segment of the conduit;

generating a fifth signal representative of the flow rate of the hydrocarbon stream in the conduit;

generating a sixth signal representative of the density of the hydrocarbon stream;

directing the first, second, third, fourth, fifth and sixth signals to computing means for executing a program for determining a first dynamic viscosity ($v_1$) of the hydrocarbon stream and a second dynamic viscosity ($v_2$) of the hydrocarbon stream, each one of the dynamic viscosities being defined by:

$$\mu = \frac{1.472 * 10^5 d^4 \Delta p}{QL}$$

where $\mu$=dynamic viscosity, cP, d=inner dia of conduits, mm,

L=length of segments, mm,

Q=flow rate in conduits, ml/min, and $\Delta p$=press drop across segments, bars;

converting dynamic viscosities to kinematic viscosities;

using ASTM D341 equations stored in a memory of the computing means, extrapolating the first kinematic viscosity to one of 40° C. and 100° C. and extrapolating the second kinematic viscosity to the other of 40° C. and 100° C., using ASTM D2270 basic values for L and H for kinematic viscosity in 40°–100° C. system stored in the memory of the computing means, determining the VI of said hydrocarbon stream in accordance with:

$$VI = \frac{L - U}{L - H} * 100$$

wherein

L=v at 40° C. of the VI 0 oil, cSt or mm$^2$/s,

H=v at 40° C. of the VI 100 oil, cSt or mm$^2$/s, and

U=v at 40° C. of said liquid hydrocarbon stream, cSt or mm$^2$/s; and with said computing means, generating a signal representative of the VI of said liquid hydrocarbon stream.

4. A system for continuously measuring the viscosity index (VI) of liquid hydrocarbon stream comprising:

means for feeding a said hydrocarbon stream through a first conduit;

means for generating a first signal representative of the temperature of the stream in the first conduit;

means for generating a second signal representative of the pressure drop ($\Delta p1$) across at least a segment of the length of said first conduit;

means for changing the temperature of the stream;

means for feeding said hydrocarbon stream through a second conduit;

means for generating a third signal representative of the temperature of the stream in said second conduit;

means for generating a fourth signal representative of the pressure drop ($\Delta p2$) across at least a segment of the length of said second conduit;

means for directing the first, second, third and fourth signals to computing means for executing a program to determine a slope in response to the first, second, third and fourth signals;

means, with said computing means and from said slope, for generating a signal representative of the VI of said liquid hydrocarbon stream.

5. The system of claim 4 wherein said slope is defined by:

$$\text{slope} = \frac{\log \Delta p_1 - \log \Delta p_2}{1/T_1 - 1/T_2}$$

wherein $\Delta p_1$=pressure drop-first conduit (bars),

Δp₂=pressure drop-second conduit (bars),
T₁=absolute temperature-first slip-stream portion,
T₂=absolute temperature-second slip-stream portion.

6. A system for continuously measuring the viscosity index (VI) of a liquid hydrocarbon stream comprising:

means for feeding said hydrocarbon stream through a first segment of a conduit;

means for generating a first signal representative of a temperature ($T_1$) of the stream in said first segment;

means for generating a second signal representative of the pressure drop (Dp1) across at least a portion of the first segment of the conduit;

means for changing the temperature of the hydrocarbon stream;

means for feeding the hydrocarbon stream through a second segment of the conduit;

means for generating a third signal representative of the temperature ($T_2$) of the hydrocarbon stream in the second segment;

means for generating a fourth signal representative of the pressure drop (Dp2) across at least a portion of the second segment of the conduit;

means for generating a fifth signal representative of the flow rate of the hydrocarbon stream in the conduit;

means for generating a sixth signal representative of the density of the hydrocarbon stream;

computing means responsive to the first, second, third, fourth, fifth and sixth signals for executing a program to calculate a first dynamic viscosity ($v_1$) of the hydrocarbon stream and a second dynamic viscosity ($v_2$) of the hydrocarbon stream, each one of the dynamic viscosities being defined by:

$$v = \frac{[1.45]\underline{1.472} * 10^5 d^4 Dp}{QL}$$

wherein v=dynamic viscosity, [cSt or mm2/s] cP, d=inner dia of conduits, mm,

L=length of segments, mm,

Q=flow rate in conduits, ml/min, and

Dp=press drop across segments, bars;

means for converting dynamic viscosities to kinematic viscosities;

said computing means extrapolating the first kinematic viscosity to one of 40° C. and 100° C. and extrapolating the second kinematic viscosity to the other of 40° C. and 100° C. in accordance with ASTM D341 equations stored in a memory, said computing means, using ASTM D2270 tabulated basic values for L and H for kinematic viscosity in 40°–100° C. system stored in the memory, determining the VI of said hydrocarbon stream in accordance with:

$$VI = \frac{L - U}{L - H} * 100$$

wherein

L=v at 40° C. of the VI 0 oil, cSt or mm²/s,

H=v at 40° C. of the VI 100 oil, cSt or mm²/s, and

U=v at 40° C. of said liquid hydrocarbon stream, cSt or mm²/s;

and with said computing means, generating a signal representative of the VI of said liquid hydrocarbon stream.

* * * * *